United States Patent
Horton et al.

(10) Patent No.: US 11,931,713 B2
(45) Date of Patent: Mar. 19, 2024

(54) OLIGONUCLEOTIDE DATA STORAGE ON SOLID SUPPORTS

(71) Applicant: Global Life Sciences Solutions Operations UK Ltd, Sheffield (GB)

(72) Inventors: Jeffrey Kenneth Horton, Cardiff (GB); Peter James Tatnell, Cardiff (GB); Robert Stone, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 661 days.

(21) Appl. No.: 15/102,209

(22) PCT Filed: Nov. 26, 2014

(86) PCT No.: PCT/EP2014/075708
§ 371 (c)(1),
(2) Date: Jun. 6, 2016

(87) PCT Pub. No.: WO2015/090879
PCT Pub. Date: Jun. 25, 2015

(65) Prior Publication Data
US 2017/0151545 A1    Jun. 1, 2017

(30) Foreign Application Priority Data

Dec. 18, 2013  (GB) ..................... 1322400

(51) Int. Cl.
*B01J 19/00*     (2006.01)
*C12Q 1/68*     (2018.01)
*C12Q 1/6874*   (2018.01)

(52) U.S. Cl.
CPC .......... *B01J 19/0046* (2013.01); *C12Q 1/68* (2013.01); *C12Q 1/6874* (2013.01); *B01J 2219/00529* (2013.01); *B01J 2219/00596* (2013.01); *B01J 2219/00722* (2013.01)

(58) Field of Classification Search
None
See application file for complete search history.

(56) References Cited

U.S. PATENT DOCUMENTS

2004/0014068 A1 * 1/2004 Burgoyne ............ C12Q 1/6806
435/6.11

FOREIGN PATENT DOCUMENTS

| WO | 90/03959 A1 | 4/1990 |
|---|---|---|
| WO | 96/39813 A1 | 12/1996 |
| WO | 00/14505 A1 | 3/2000 |
| WO | 03/025123 A2 | 3/2003 |
| WO | 2013/178801 A2 | 12/2013 |

OTHER PUBLICATIONS

Tan et al., "DNA, RNA and Protein Extraction: The Past and The Present" (Jul. 2009) Journal of Biomedicine and Biotechnology, vol. 2009 pp. 1-10.*
ScienceProfOnline, "How to Prepare a Microscope Slide of Bacteria," downloaded Jul. 19, 2022 from (https://www.scienceprofonline.com/microbiology/how-to-prepare-microscope-slide-of-bacteria.html), 5 pages (Year: 2012).*
Goldman et al., "Towards Practical, high-capacity, low-maintenance information storage in synthesized DNA", Nauture, Jan. 1, 2013, 4 pages.
Church et al., "Next-Generation Digital Information Storage in DNA", Science, vol. 337, No. 6102, Sep. 28, 2012, 2 pages.
International Search Report and Written Opinion regarding International Application No. PCT/EP2014/075708, dated Mar. 12, 2015, 10 pages.
GE Healthcare Application note 28-9822-24 AA, "Comparative analysis of FTA and Nucleosave cards", Dec. 2010: Available online: https://www.gelifesciences.com/gehcls_images/GELS/Related%20Content/Files/1314807262343/itdoc28982224_20130905165433.pdf, 8 pages.
GE Healthcare Application note 28-9822-24 AA, "Reliable extraction of DNA from Whatman FTA cards", Oct. 2010: Available online: https://www.gelifesciences.com/gehcls_images/GELS/Related%20Content/Files/1392818611307/litdoc28982222_20140311044843.pdf, 8 pages.
GB Search Report regarding GB Application No. GB1322400.1, dated Sep. 5, 2014, 3 pages.

* cited by examiner

*Primary Examiner* — G. Steven Vanni
(74) *Attorney, Agent, or Firm* — Eversheds Sutherland (US) LLP

(57) ABSTRACT

A data storage medium is disclosed comprising a solid support matrix including an optional stabilising reagent or reagents in a dry form, for use as a support for artificially synthesised oligonucleotide sequences encoded with data. Preferably the matrix is fibrous (for example cellulose, or glass, fibres) formed into a support of sufficient strength to hold the oligonucleotide sequences. The stabilising reagents are preferably a combination of a weak base, and a chelating agent, optionally, uric acid or a urate salt, and optionally an anionic surfactant.

21 Claims, 4 Drawing Sheets
Specification includes a Sequence Listing.

GCGCCCAATA CGCAAACCGC CTCTCCCCGC GCGTTGGCCG ATTCATTAAT GCAGCTGGCA
CGACAGGTTT CCCGACTGGA AAGCGGGCAG TGAGCGCAAC GCAATTAATG TGAGTTAGCT
CACTCATTAG GCACCCCAGG CTTTACACTT TATGCTTCCG GCTCGTATGT TGTGTGGAAT
TGTGAGCGGA TAACAATTTC ACACAGGAAA CAGCTATGAC CATGATTACG CCAAGCTTGC
ATGCCTGCAG GTCGACTCTA GAGGATCCCC TCCGTCTGGG CTTCTTGCAT TCTGGGACAG
CCAAGTCTGT GACTTGCACG TACTCCCTG CCCTCAACAA GATGTTTTGC CAACTGGCCA
AGACCTGCCC TGTGCAGCTG TGGGTTGATT CCACACCCCC GCCCGGCACC CGCGTCCGCG
CCATGGCCAT CTACAAGCAG TCACAGCACA TGACGGAGGT TGTGAGGCGC TGCCCCCACC
ATGAGCGCTG CTCAGATAGC GATGGTCTGG CCCCTCCTCA GCATCTTATC CGAGTGGAAG
GAAATTTGCG TGTGAGTAT TTGGATGACA GAAACACTTT TCGACATAGT GTGGTGGTGC
CCTATGAGCC GCCTGAGGTT GGCTCTGACT GTACCACCAT CCACTACAAC TACATGTGTA
ACAGTTCCTG CATGGGCGGC ATGAACCGGA GGCCCATCCT CACCATCATC ACACTGGAAG
ACTCCAGTGG TAATCTACTG GGACGGAACA GCTTTGAGGT GCGTGTTTGT GCCTGTCCTG
GGAGAGACCG GCGCACAGAG GAAGAGAATC TCCGCAAGAA AGGGGAGCCT CACCACGAGC
TGCCCCCAGG GAGCACTAAG CGAGCACTGC CCAACAACAC CAGCTCCTCT CCCCAGCCAA
AGAAGAAACC ACTGGATGGA GAATATTTCA CCCTTCAGAT CCGTGGGCGT GAGCGCTTCG
AGATGTTCCG AGAGCTGAAT GAGGCCTTGG AACTCAAGGA TGCCCAGGCT GGGAAGGAGC
CAGGGGGGAG CAGGGCTCAC TCCAGCCACC TGAAGTCCAA AAAGGGTCAG TCTACCTCCC
GGGTACCGAG CTCGAATTCA CTGGCCGTCG TTTTACAACG TCGTGACTGG GAAAACCCTG
GCGTTACCCA ACTTAATCGC CTTGCAGCAC ATCCCCCTTT CGCCAGCTGG CGTAATAGCG
AAGAGGCCCG CACCGATCGC CCTTCCCAAC AGTTGCGCAG CCTGAATGGC GAATGGCGCC
TGATGCGGTA TTTTCTCCTT ACGCATCTGT GCGGTATTTC ACACCGCATA TGGTGCACTC
TCAGTACAAT CTGCTCTGAT GCCGCATAGT TAAGCCAGCC CCGACACCCG CCAACACCCG
CTGACGCGCC CTGACGGGCT TGTCTGCTCC CGGCATCCGC TTACAGACAA GCTGTGACCG
TCTCCGGGAG CTGCATGTGT CAGAGGTTTT CACCGTCATC ACCGAAACGC GCGAGACGAA
AGGGCCTCGT GATACGCCTA TTTTTATAGG TTAATGTCAT GATAATAATG GTTTCTTAGA
CGTCAGGTGG CACTTTTCGG GGAAATGTGC GCGGAACCCC TATTTGTTTA TTTTTCTAAA
TACATTCAAA TATGTATCCG CTCATGAGAC AATAACCCTG ATAAATGCTT CAATAATATT
GAAAAAGGAA GAGTATGAGT ATTCAACATT TCCGTGTCGC CCTTATTCCC TTTTTTGCGG
CATTTTGCCT TCCTGTTTTT GCTCACCCAG AAACGCTGGT GAAAGTAAAA GATGCTGAAG
ATCAGTTGGG TGCACGAGTG GGTTACATCG AACTGGATCT CAACAGCGGT AAGATCCTTG
AGAGTTTTCG CCCCGAAGAA CGTTTTCCAA TGATGAGCAC TTTTAAAGTT CTGCTATGTG
GCGCGGTATT ATCCGTATT GACGCCGGGC AAGAGCAACT CGGTCGCCGC ATACACTATT
CTCAGAATGA CTTGGTTGAG TACTCACCAG TCACAGAAAA GCATCTTACG GATGGCATGA
CAGTAAGAGA ATTATGCAGT GCTGCCATAA CCATGAGTGA TAACACTGCG GCCAACTTAC
TTCTGACAAC GATCGGAGGA CCGAAGGAGC TAACCGCTTT TTTGCACAAC ATGGGGGATC
ATGTAACTCG CCTTGATCGT TGGGAACCGG AGCTGAATGA AGCCATACCA AACGACGAGC
GTGACACCAC GATGCCTGTA GCAATGGCAA CAACGTTGCG CAAACTATTA ACTGGCGAAC
TACTTACTCT AGCTTCCCGG CAACAATTAA TAGACTGGAT GGAGGCGGAT AAAGTTGCAG
GACCACTTCT GCGCTCGGCC CTTCCGGCTG GCTGGTTTAT TGCTGATAAA TCTGGAGCCG
GTGAGCGTGG GTCTCGCGGT ATCATTGCAG CACTGGGGCC AGATGGTAAG CCCTCCCGTA

FIG. 1

```
TCGTAGTTAT CTACACGACG GGGAGTCAGG CAACTATGGA TGAACGAAAT AGACAGATCG
CTGAGATAGG TGCCTCACTG ATTAAGCATT GGTAACTGTC AGACCAAGTT TACTCATATA
TACTTTAGAT TGATTTAAAA CTTCATTTTT AATTTAAAAG GATCTAGGTG AAGATCCTTT
TTGATAATCT CATGACCAAA ATCCCTTAAC GTGAGTTTTC GTTCCACTGA GCGTCAGACC
CCGTAGAAAA GATCAAAGGA TCTTCTTGAG ATCCTTTTTT TCTGCGCGTA ATCTGCTGCT
TGCAAACAAA AAAACCACCG CTACCAGCGG TGGTTTGTTT GCCGGATCAA GAGCTACCAA
CTCTTTTTCC GAAGGTAACT GGCTTCAGCA GAGCGCAGAT ACCAAATACT GTTCTTCTAG
TGTAGCCGTA GTTAGGCCAC CACTTCAAGA ACTCTGTAGC ACCGCCTACA TACCTCGCTC
TGCTAATCCT GTTACCAGTG GCTGCTGCCA GTGGCGATAA GTCGTGTCTT ACCGGGTTGG
ACTCAAGACG ATAGTTACCG GATAAGGCGC AGCGGTCGGG CTGAACGGGG GGTTCGTGCA
CACAGCCCAG CTTGGAGCGA ACGACCTACA CCGAACTGAG ATACCTACAG CGTGAGCTAT
GAGAAAGCGC CACGCTTCCC GAAGGGAGAA AGGCGGACAG GTATCCGGTA AGCGGCAGGG
TCGGAACAGG AGAGCGCACG AGGGAGCTTC CAGGGGGAAA CGCCTGGTAT CTTTATAGTC
CTGTCGGGTT TCGCCACCTC TGACTTGAGC GTCGATTTTT GTGATGCTCG TCAGGGGGC
GGAGCCTATG GAAAAACGCC AGCAACGCGG CCTTTTTACG GTTCCTGGCC TTTTGCTGGC
CTTTTGCTCA CATGTTCTTT CCTGCGTTAT CCCCTGATTC TGTGGATAAC CGTATTACCG
CCTTTGAGTG AGCTGATACC GCTCGCCGCA GCCGAACGAC CGAGCGCAGC GAGTCAGTGA
GCGAGGAAGC GGAAGA
```

FIG. 1 (continued)

```
CAGGAAACAG CTATGACCAT GATTACGCCA AGCTTGCATG CCTGCAGGTC GACTCTAGAG
GATCCCCTCC GTCTGGGCTT CTTGCATTCT GGGACAGCCA AGTCTGTGAC TTGCACGTAC
TCCCCTGCCC TCAACAAGAT GTTTTGCCAA CTGGCCAAGA CCTGCCCTGT GCAGCTGTGG
GTTGATTCCA CACCCCCGCC CGGCACCCGC GTCCGCGCCA TGGCCATCTA CAAGCAGTCA
CAGCACATGA CGGAGGTTGT GAGGCGCTGC CCCCACCATG AGCGCTGCTC AGATAGCGAT
GGTCTGGCCC CTCCTCAGCA TCTTATCCGA GTGGAAGGAA ATTTGCGTGT GGAGTATTTG
GATGACAGAA ACACTTTTCG ACATAGTGTG GTGGTGCCCT ATGAGCCGCC TGAGGTTGGC
TCTGACTGTA CCACCATCCA CTACAACTAC ATGTGTAACA GTTCCTGCAT GGGCGGCATG
AACCGGAGGC CCATCCTCAC CATCATCACA CTGGAAGACT CCAGTGGTAA TCTACTGGGA
CGGAACAGCT TTGAGGTGCG TGTTTGTGCC TGTCCTGGGA GAGACCGGCG CACAGAGGAA
GAGAATCTCC GCAAGAAAGG GGAGCCTCAC CACGAGCTGC CCCCAGGGAG CACTAAGCGA
GCACTGCCCA ACAACACCAG CTCCTCTCCC CAGCCAAAGA AGAAACCACT GGATGGAGAA
TATTTCACCC TTCAGATCCG TGGGCGTGAG CGCTTCGAGA TGTTCCGAGA GCTGAATGAG
GCCTTGGAAC TCAAGGATGC CCAGGCTGGG AAGGAGCCAG GGGGAGCAG GGCTCACTCC
AGCCACCTGA AGTCCAAAAA GGGTCAGTCT ACCTCCCGGG TACCGAGCTC GAATTCACTG
GCCGTCGTTT TAC
```

FIG. 2

```
GCGCACAGAG GAAGAGAATC TCCGCAAGAA AGGGGAGCCT CACCACGAGC TGCCCCCAGG
GAGCACTAAG CGAGCACTGC CCAACAACAC CAGCTCCTCT CCCCAGCCAA AGAAGAAACC
ACTGGATGGA GAATATTTCA CCCTTCAGAT CCGTGGGCGT GAGCGCTTCG AGATGTTCCG
AGAGCTGAAT GAGGCCTTGG
```

FIG. 3

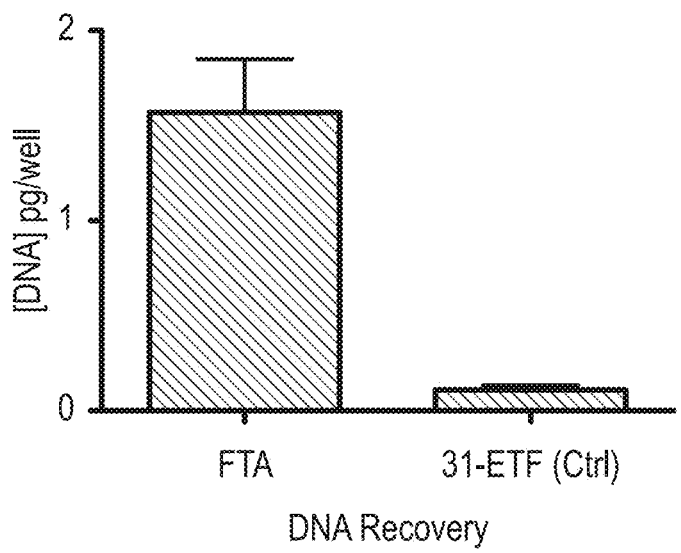

FIG. 4

OLIGONUCLEOTIDE DATA STORAGE ON SOLID SUPPORTS

CROSS-REFERENCE TO RELATED APPLICATIONS

This application is a filing under 35 U.S.C. 371 of international application number PCT/EP2014/075708, filed Nov. 26, 2014, which claims priority to GB application number 1322400.1, filed Dec. 18, 2013, the entire disclosures of each of which are hereby incorporated by reference.

BACKGROUND OF THE INVENTION

Field of the Invention

The present invention relates to the storage and retrieval of data in the form of stabilised oligonucleotide nucleic acids.

Description of the Related Art

Publications referred to herein are incorporated by reference in their entirety.

The problem associated with storing the large volumes of data generated, is an ever-growing challenge. It is no longer feasible to store large amounts of data on a paper hard copy. Digital technology provides a better solution but even the presently used forms of digital data storage have their limits. As increasing amounts of data, and more complex forms of information are created; storing these data using known digital media presents many difficulties. For example, computer hard drives and servers have limited capacity and require power and maintenance, while magnetic data storage media degrades. Very long term storage is also problematic with known digital storage media, because, as well as the problems mentioned above, they can readily be affected by natural disasters and strong electromagnetic pulses for example from atomic weapon reactions or as occurs beyond Earth's atmosphere. There are also physical limits to the size of the equipment needed to store electronic data, meaning that it is becoming more and more problematic to accommodate this equipment.

Church; Gao; and Kosuri (2012). "Next-Generation Digital Information Storage in DNA". Science 337 (6102): 1628. [doi:10.1126/science.1226355] suggest that DNA can be artificially synthesised in a form which encodes digital data. It is reported that DNA was encoded with digital information that included an HTML draft of a 53400 word book, as well as JPEG images and a java script algorithm. However, issues with errors were reported.

Further, Goldman; Bertone; Chen; Dessimoz; Leproust; Birney (2013). "Towards practical, high-capacity, low-maintenance information storage in synthesized DNA". Nature 494 (7435): 77-80. [doi:10.1038/nature11875] report that DNA in the form of synthesised oligonucleotides could be prepared in a sequence which could then be read later. Successful retrieval of that DNA data was reported also with no final errors, apparently because much of the DNA sequence data was overlapping, so intermediate errors could be identified and ignored. A sequential encoding technique was employed also to reduce errors. Since the synthesised oligonucleotides occupied very little volume, it was demonstrated that this technique could provide very high data density, and thereby be an answer to holding ever-increasing volumes of data. In more detail, the authors were able to write and retrieve hours of high-definition video information using DNA sequences. The DNA was synthesized with defined sequence the order of which was indicative of the encoded digital information. In the study, 739 kilobytes of hard-disk information in the form of a MP3 of Martin Luther King's 'I have a dream' speech, a photo of European Bioinformatics Institute in jpeg form, a text file of all of William Shakespeare's sonnets and a pdf of James Watson & Francis Crick's paper on the structure of DNA were taken and the digital information were all transformed into many overlapping complementary synthetically generated oligonucleotide DNA strands (~100 bps in length). The multiple DNA strands were subsequently sequenced, reassembled and the digital information successfully recovered with 100% accuracy.

However, no thought was given by Church or Goldman et al to the long term storage of the DNA used to hold the data. Since DNA is in essence a string of monomers formed from nucleic acids, then like all organic matter, it can degrade, particularly in the presence of enzymes, bacteria and moulds. It has been found that given ideal, cold, dry and dark conditions naturally occurring DNA can last for tens of thousands of years, for example as demonstrated by the DNA found within the remains of frozen woolly mammoths and the like. So, naturally it would be possible to keep the sequenced oligonucleotide data in cool, dry and dark conditions with a reasonable chance of preserving it for long periods. The problem with that approach is that in most parts of the developed world, cool, dry and dark conditions require power and maintenance, which may not be available long term, for example due to natural disasters or wars. Moreover, important data will require more certainty that the data will be preserved. So what is required is some form of physical storage arrangement which does not rely on power, and which is certain to keep the sequenced oligonucleotides in good condition, for subsequent decoding and reading of the data they contain. Further, it is postulated that the relatively short sequenced oligonucleotides used by Goldman et al to hold data may be less stable than the relatively long DNA sequences occurring in nature, and so their successful long term storage may need more than the cool dry and dark conditions mentioned above.

SUMMARY OF THE INVENTION

The inventors of the present invention have realised that a solution to the above problem can be found in the use of a solid support matrix to which support can be applied oligonucleotide sequences in the form of artificially synthesised DNA encoded with data, preferably according to the description below. Preferably the solid support includes a dried stabilising chemical. In particular they have found that a cellulose fibre paper and chemical coating on the paper (described in more detail below) sold under the trade name FTA (by Whatman Inc) provides a superior storage medium for oligonucleotides of about the length used by Goldman et al and longer.

Another issue is the monitoring of data integrity. The inventors propose herein a method and apparatus to facilitate visual monitoring of the DNA integrity and also a method and apparatus for monitoring DNA integrity by means of processing. These methods and apparatus will have applications beyond storage of data encoded in DNA and can be used for monitoring the integrity of naturally occurring DNA also.

According to a first aspect the invention provides a data storage medium comprising a solid support matrix for use as a dry storage support for oligonucleotide sequences encoded with data.

In an embodiment, said matrix includes a stabilising reagent or reagent mix in a dry form.

In an embodiment, the matrix is fibrous (for example cellulose, or glass, fibres) formed into a support of sufficient strength to hold the oligonucleotide sequences.

In an embodiment, the stabilising reagent or reagent mix is a reagent mix and comprises a combination of a weak base, and a chelating agent, optionally, uric acid or a urate salt, and optionally an anionic surfactant.

In an embodiment, the weak base is a Lewis base which has a pH of about 6 to 10, preferably about pH 8 to 9.5.

In an embodiment, the weak base is an organic and inorganic base, and if inorganic then optionally includes an alkali metal carbonate, bicarbonate, phosphate or borate (e.g. sodium, lithium, or potassium carbonate), and if organic then optionally includes, tris-hydroxymethyl amino methane (Tris), ethanolamine, tri-ethanolamine and glycine and alkaline salts of organic acids (e.g. trisodium citrate).

In an embodiment, the weak base is Tris present either as a free base or as a salt, for example, a carbonate salt.

In an embodiment, the chelating agent binds multivalent metal ions with a comparable or better affinity than ethylene diamine tetraacetic acid (EDTA), and is preferably EDTA.

In an embodiment, the anionic surfactant includes a hydrocarbon moiety, aliphatic or aromatic, containing one or more anionic groups.

In an embodiment, the anionic surfactant is a detergent, for example sodium dodecyl sulphate (SDS) and/or sodium lauryl sarcosinate (SLS).

In an embodiment, the stabilising reagent comprises a chaotropic substance such as a chaotropic salt, for example guanidinium thiocyanate.

In an embodiment, the storage medium includes a visual delineation around an area holding DNA data for example a printed boundary showing where the DNA is stored, or an indicating dye such as chlorophenol red or phenol red, which discolour, thereby showing where the DNA is stored.

According to a second aspect the invention provides a method of storing data, said method comprising the following steps: a) producing synthesised oligonucleotides having an nucleotide sequence representative of data to be stored; b) optionally replicating said oligonucleotides; and c) depositing said oligonucleotides, optionally replicated, onto a storage medium according to the first aspect.

In an embodiment, at least steps b) and c) are performed in a liquid, and said liquid is allowed or caused to evaporate from the storage medium.

In an embodiment, step a) is performed according instructions published in the Goldman paper referred to herein.

Alternatively, step a) includes converting binary data into a quaternary code, and sequencing DNA nucleotides, according to the quaternary code to provide said oligonucleotides.

In an embodiment, said conversion follows the n+1 rule described herein.

In an embodiment, wherein step a) includes incorporating a reporter into said sequence, to provide an indication of data integrity, optionally said reporter providing an increase or decrease in detectability in response to a change in said integrity.

Preferably, said reporter is a fluorescent dye.

In an embodiment, said nucleotide sequence is at least 250 base pairs in length, and preferably at least about 1000 base pairs, for example at least about 963 base pairs.

In an embodiment, said replication is by means of a polymerase chain reaction (PCR), isothermal amplification, or rolling circle amplification.

In an embodiment, one or more sequences which aid replication are added to the end or ends of the sequenced oligonucleotides.

According to a third aspect, the invention provides a method for recovering stored data from the storage medium of the first aspect when stored according to the method of the second aspect, said recovery method comprising the steps of: i) extracting at least a portion of the replicated oligonucleotides from the storage medium; ii) optionally performing further replication of said oligonucleotides; and iii) performing an analysis of the oligonucleotides to determine their nucleotide sequence, and decoding said sequence to thereby to recover said stored data.

In an embodiment, said extracting step includes removing at least a portion of the storage medium, introducing into a vessel the at least a portion, and then performing said further replication step.

In an embodiment, said further replication step includes: adding a liquid to said at least a portion.

In an embodiment, the analysis step includes determining the nucleic composition of the oligonucleotide by known techniques, for example using: an electropherogram; radio-labelling; single-molecule real-time sequencing (Pacific Biosciences, SMRT, Oxford Nannpore); ion semiconductor (Ion Torrent [Life Technologies]); pyrosequencing (454 Life Sciences [Rouche]); sequencing by synthesis (Illumina); sequencing by ligation (SOLiD Systems[Applied Biosystems]); dideoxy chain termination (Sanger sequencing).

According to a third aspect the invention provides a method for determining the integrity of DNA stored on a storage medium, for example a storage medium according to the first aspect, said method including the steps of: 1) performing an STR profile analysis on a portion of the DNA stored; or 2) using a reporter incorporated into the DNA sequence to assess said integrity, for example where said reporter fluoresces, or stops fluorescing when said integrity is reduced.

The invention is further characterised by the claims.

BRIEF DESCRIPTION OF THE DRAWINGS

FIG. 1 shows a Oligonucleotide sequenced as deposited on an FTA card—(sequence listing 1);

FIG. 2 shows a portion of the sequence of FIG. 1 recovered from an FTA card—(sequence listing 2);

FIG. 3 shows another portion of the sequence of FIG. 1 recovered from an FTA card—(sequence listing 3);

FIG. 4 shows a comparison between recovery using FTA cards and plain paper;

DETAILED DESCRIPTION OF THE INVENTION

Figure 5:
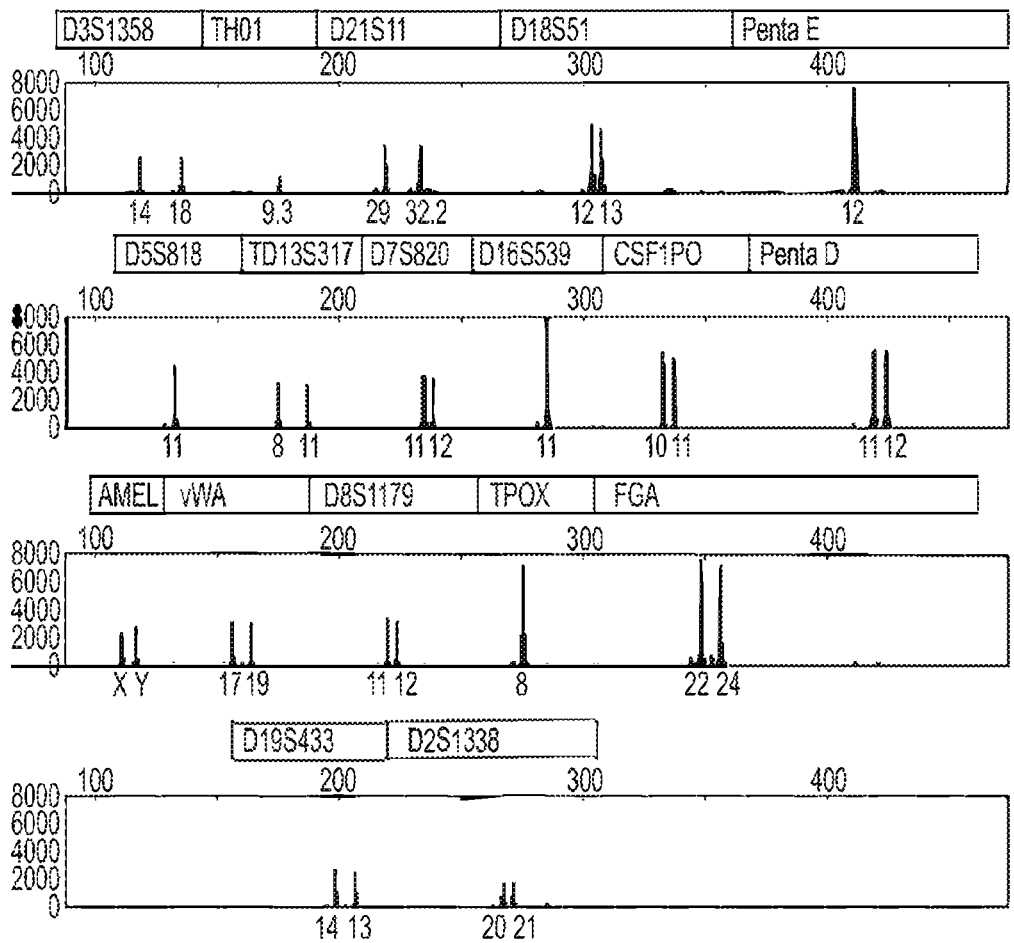
FIG. 5 shows the results of a DNA integrity experiment using STR profiling.

In one embodiment digital information is encoded into sequenced DNA according to directions given in Goldman et al 2013. This group used a number of common computer file formats. In this case, five files comprised all 154 of Shakespeare's sonnets (ASCII text), a classic scientific paper, a medium-resolution colour photograph of the European Bioinformatics Institute (JPEG), a 26-second excerpt from Martin Luther King's 1963 'I have a dream' speech (MP3 format). The data comprising each file were represented as DNA information sequences (see FIG. 1) known as base pairs (bp) formed from the known constituents of DNA namely Adenine (A), Cytosine (C), Guanine (G) and Thymine (T). Each DNA sequence was split into overlapping segments, generating fourfold redundancy, and alternate segments were converted to their reverse complement. These measures reduce the probability of data loss. Each segment was augmented with indexing information that facilitated the identification of the file from which it originated and its location within that file. In all, the five files were represented by a total of 153,335 segments of DNA information, each comprising 117 nucleotides bps. Oligonucleotides were synthesised corresponding to the designed DNA segments, creating $1.2 \times 10^7$ copies of each oligonucleotide. Errors occur independently during synthesise (1 error per 500 bases) in the different copies of each string. Thus reducing the method's overall error rate. After resuspension, amplification and purification, a sample of the resulting library was sequenced to recover the information. The remainder was sub-aliquoted and re-lyophilized for long-term storage typically at minus 20° Celsius. Sequencing results yielded $79.6 \times 10^6$ read-pairs of 104 bases in length, from which the authors reconstructed full-length (117-nt) oligonucleotides in silico. Full-length DNA sequences representing the original encoded files were then reconstructed digitally using software looking for the indexing information. The resulting DNA sequences could be fully decoded without intervention. Inspection confirmed that the original computer files had been reconstructed with 100% accuracy.

Goldman transposed digital binary computer information into ternary (base 3), requiring just three characters, and then encoded that information into the DNA. This allows the four nucleotide bases (A, C, G, and T) to represent 0, 1, and 2 sequentially with 1 redundant base, and thus avoid repetitive use of bases which can cause data recovery errors due to present day sequencing machine shortcomings. For example, at one base A=0, C=1 and G=2, if the next base would be repeated then, for the next base C=0, G=1 and T=2, and so on. This ensures that a sequence of identical digits in the data is not represented by a sequence of identical bases in the DNA, helping to avoid reading mistakes.

Alternatively, a quaternary (base 4) system is proposed here, with or without the shifting base representation system mentioned immediately above. Conveniently, quaternary codes of 4 characters (A, C, G and T) provide a binary 8 bit byte (octet). ASCII code requires 7 bits, and a parity bit can be added to each character to provide error detection.

In a quaternary based system, the following encoding may be used:

difficult to read. The use of a quaternary system is not tied to the use of ASCII characters, and so any binary code can be transposed into base pairs according to the steps in the table above.

Recovering the data is possible by reversing the encoding shown in the table.

The DNA data storage medium of the present invention is based on a product known as FTA® as supplied by GE Healthcare Inc, and variants of that product, for example FTA Elute, the compositions of which are given in more detail below, and which are herein referred to generally as FTA or FTA cards or FTA paper.

FTA includes stabilising reagent mix which comprises a combination of a weak base, and a chelating agent, optionally, uric acid or a urate salt, and optionally an anionic surfactant.

The "weak base" of the combination may be a Lewis base which has a pH of about 6 to 10, preferably about pH 8 to 9.5. One function of the weak base is to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, tri-ethanolamine and glycine and alkaline salts of organic acids (e.g. trisodium citrate). A preferred organic weak base is a weak monovalent organic base, for example, Tris. The Tris may be either a free base or a salt, for example, a carbonate salt.

A preferred chelating agent is a strong chelating agent. By "strong" chelating agent it is meant that the agent binds multivalent metal ions with a comparable or better affinity than ethylene diamine tetraacetic acid (EDTA). A preferred chelating agent according to the invention is EDTA.

Anionic surfactants are examples of surfactants which are useful in the present invention. A preferred anionic surfactant is a strong anionic detergent. As used herein, a "strong" anionic detergent includes a hydrocarbon moiety, aliphatic or aromatic, containing one or more anionic groups. Particularly preferred anionic detergents suitable for the invention include sodium dodecyl sulphate (SDS) and sodium lauryl sarcosinate (SLS). In a preferred embodiment, the

```
English language characters                                 G E

ASCII 7 bit code plus parity bit                            10001111 10001010

Quaternary code                                             2033 2022

DNA sequence [where A = 0, C = 1,                           GATT GAGG
G = 2 and T = 3 always]

DNA sequence [where n + 1 is used, according to the         GTCA GTAT
following rule:]
Previous bases                      Next bases
A = 0, C = 1, G = 2 and T = 3       A = 1, C = 2, G = 3 and T = 0
A = 1, C = 2, G = 3 and T = 0       A = 2, C = 3, G = 0 and T = 1
A = 2, C = 3, G = 0 and T = 1       A = 3, C = 0, G = 1 and T = 2
A = 3, C = 0, G = 1 and T = 2       A = 0, C = 1, G = 2 and T = 3
```

The n+1 quaternary system used above increases data density over the ternary system used by Goldman, but still reduces the chances of strings of repeating bases which are anionic detergent causes inactivation of most microorganisms which have protein or lipids in their outer membranes or capsids, for example, fungi, bacteria or viruses. This includes microorganisms which may be pathogenic to humans and are present in a biological sample. The detergent also functions to denature proteins such as DNAses thereby affording additional protection to the applied DNA. The storage medium has a visual delineation (to the human eye or an automated device such as a camera and controller) around an area holding DNA data so that it is possible in future to view where the DNA was deposited. In this case the delineation is a printed circle into which the DNA is deposited, but an indicating dye can also provide a delineation.

Alternatively, a product called FTA Ellute could be used as a storage medium, in which case the stabilising reagent may comprise a single reagent, for example a chaotropic substance such as a chaotropic salt, for example guanidinium thiocyanate.

In order to demonstrate that a viable long term storage solution could be achieved a data storage medium in the form of a solid support matrix including a stabilising reagent or reagents in a dry form, for use as a support for oligonucleotide sequences encoded with data, 2 experiments were performed:

Example 1

Sequencing of DNA Fragments Applied to FTA Cards

Samples of plasmid DNA designated pUC19-p53 were spotted (stock concentration of 0.5 µg/ml in TE buffer) at a 1 ng mass onto FTA sample collection cards (GE Healthcare). These cards provide stabilising reagents according to the invention. This plasmid contains a 1038 base pairs of a gene named p53 mRNA co-corresponding to nucleotide sequence from 217 to 1255 of the p53 cDNA as described in GenBank accession number BC003596 (IMAGE; 3544714, MGC; 646). This fragment was cloned into the SmaI site of the plasmid pUC19. The DNA sequence of the pUC-p53 DNA prior to application to FTA is shown in FIG. 1. After application of the plasmid, the FTA cards were left to air dry for 60 min before being placed into multi-barrier pouches and stored at room temperature for at least a week (as recommended by the manufacturer).

DNA was extracted from the sample collection matrices using an Illustra™ tissue and cells genomic prep Mini Spin Kit (GE Healthcare) according to manufacturer's recommendations with modifications as outlined below.
1. The 3.0 mm marked disk containing the applied DNA sample was removed using a Uni-Core punch and placed into a 1.5 ml sterile tube.
2. Sterile phosphate buffered saline (PBS) (1 ml) was added to each tube.
3. Tubes were centrifuged at 12 000 rpm for 2 min (All centrifugations were conducted in a Heraeus Biofuge™).
4. PBS was discarded and 50 µl of fresh sterile PBS was added to each tube.
5. The 3.0 mm punches were homogenized using a 20-gauge sterile needle.
6. Tubes were centrifuged at 5000 rpm for 10 sec.
7. DNA was isolated from the supernatant according to the manufacturer's instructions for the Illustra tissue and cells genomic prep Mini Spin Kit.

To generate DNA for sequencing two PCR products were generated using End-Point PCR (see FIGS. 2 and 3 for details). This was carried out as follows: rTaq2 DNA Polymerase (GE Healthcare) was used together with the following primer sequences to target the p53 insert in the plasmid DNA sample extracted from the respective paper matrices.

The 963 base pair PCR product 1 (FIG. 2) was generated using the following Primers (Sigma Genosys):

```
Primer 1 (M13 forward [-20]);
5'-GTAAAACGACGGCCAGT-3'

Primer 2 (M13 reverse);
5'-CAGGAAACAGCTATGAC-3'
```

The 250 base pair PCR product 2 (FIG. 3) was generated using the following Primers (Sigma Genosys):

```
Primer 3; (forward)
5'-GCGCACAGAGGAAGAGAATC-3'

Primer 4; (reverse)
5'-CCAAGGCCTCATTCAGCTCT-3'
```

A direct/punch-in PCR reaction was also performed, as an alternative procedure, in which a 1.2 mm diameter punch was used to excise a FTA disc from the card and this was placed directly into a PCR reaction supplemented with a-cyclodextrin as described in the UK patent application GB 1219137.5. The two PCR products were generated using the primers as described above.

PCR amplicons were generated using a PCR master mix (95 µl; 1 unit of enzyme, 20 pmol forward and reverse primers) and 5 µl sample (plasmid DNA extracted from the FTA cards using the Illustra Kit) were added to appropriate wells of a 96-well plate and amplified accordingly (denature 94° C., 3 min. 30 cycles of 94° C., 30 sec; 55° C., 1 min; 72° C., 2 min; final soak at 72° C., 10 min). For direct amplification from the FTA card the 5 µl DNA sample was replaced with the appropriate volume of buffer and a FTA disc.

In order to check the integrity of the amplified DNA, 10 µl volume of each PCR was loaded on a 1% agarose/TAE buffer gel (Tris, acetic acid and Ethylenediaminetetraacetic acid (EDTA)) along with DNA size standards and positive and negative (no template) PCR controls. To generate DNA sequencing reactions the PCR products and primers described above were used following the BigDye® Terminator v3.1 Cycle Sequencing Kit manufacturer's recommendations.

To remove excess PCR primers, 2 µl of ExoproSTAR (GE Healthcare) was added to 5 µl of amplified DNA in a test tube. The test tube was sealed and spun briefly to ensure its contents were at the bottom of the tube. The tube was then incubated on a PTC200 thermocycler for 15 minutes at 37° C., followed by 15 minutes at 80° C. and a hold at 4° C. The final volume of each reaction was made up to 10 µl by the addition of sterile water prior to the cycle sequencing reaction. Stock cycle sequencing mix was made up as follows:

TABLE 1

| | Sequencing mix | | |
|---|---|---|---|
| Constituent | 1x | 10x | 15x |
| Big Dye Mix | 4 µl | 40 µl | 60 µl |
| Primer(1.6 pmol/µl) | 2 µl | 20 µl | 30 µl |
| 5x Buffer | 4 µl | 40 µl | 60 µl |

Ten microliters of sequencing mix was added to each 10 µl PCR product from above. These samples were then amplified using both forward and reverse sequencing primers using the following protocol on a MJ Research PTC200 thermocycler: 96° C. 30 seconds; 50° C. 15 seconds; 60° C. 4 minutes for 25 cycles followed by a 4° C. hold on completion of the cycling. The amplified sequencing products were then processed using the Auto Seq G-50 columns: Columns were vortexed briefly, the caps loosened and the seals removed. The columns were then placed into collection tubes. The tubes were spun for 1 minute at 2000 g in an Eppendorf 5417C centrifuge and the flow through discarded. The columns were then transferred to fresh tubes and sequencing sample slowly applied to the top of the column. The tubes were spun for 1 minute at 2000×g, the eluates were collected and stored at 2-8° C. in labelled 0.2 ml PCR tubes prior to transfer to a sequencing facility for analysis.

Each product was sequenced six times. The consensus sequences of both PCR products (product 1 and 2) were compiled from all sequencing reactions performed. The sequencing results of the amplified PCR pUC-p53 products are shown in FIGS. 2 and 3. Analysis of both consensus sequences indicates a complete homology with that described in the relevant regions of sequence described in FIG. 1.

FIG. 1 shows the sequence in pUC19 containing a fragment of the p53 cDNA as it was deposited on the FTA support matrix which includes the stabilising reagents. Sequences in italics and bold refer to pUC19- and p53-specific sequences respectively. Sequences underline refers to PCR and DNA sequencing primers used in this study.

FIG. 2 shows the recovered PCR product 1 sequence, and so demonstrates that recovery of DNA sequences of at least 963 base pairs which equates to 1900 bytes (about 2 Kb) of digital information, is possible on FTA cards. Thus relatively long DNA sequences are stable in this storage format.

FIG. 3 shows the recovered PCR product 2 sequence, and so demonstrates that recovery of DNA sequences of 250 base pairs which equates to 500 bytes (about 0.5 Kb) of digital information, is possible on FTA cards.

Example 2

Quantitative PCR (qPCR) Measurement of DNA Recovered from FTA Cards qPCR was employed to quantify the amount of amplifiable DNA on each 1.2 mm diameter disks punched from FTA cards compared with a plain paper support (Whatman product code: 31-ETF) control. The real-time PCR method targeted a 500 bp region of Lambda DNA previously applied to FTA cards and dried. The technique utilized the intercalating dye GelStar™ Nucleic Acid Stain (Lonza Group Ltd) to reveal the amplified product. This method provided the threshold cycle (Ct) values and mass amounts of amplifiable DNA when read from the standard curve. The PCR master mix contained the following components:
FideliTaq™ DNA Polymerase (GE Healthcare);
Lambda DNA (Promega Corp);
GelStar Nucleic Acid Stain, used at 1:1000 dilution in a Tris/EDTA (TE) buffer; and
Primers (Sigma Genosys):

```
Primer 1 forward
5'-GGTTATCGAAATCAGCCACAGCGCC-3'

Primer 2 reverse
5'-GATGAGTTCGTGTCCGTACAACTGG-3'
```

A PCR master mix (20 µl; containing 2.5 U enzyme, 5 pmol forward and reverse primers, and 1.5 µl GelStar Nucleic Acid Stain) and 5 µl sample or standard DNA dilution series, were added to wells of a 96-well plate and amplified on an Applied Biosystems 7900HT Fast Real-Time PCR System according to the specified cycling conditions (denature 95° C., 3 min. 40 cycles of 95° C., 30 sec; 55° C., 30 sec; 72° C., 1 min).

Data were generated using qPCR to reveal the amounts of amplifiable DNA that could be recovered from DNA-spotted FTA cards. The standard curve was used to accurately determine the amount of amplifiable DNA that could be recovered from FTA cards. Amounts of DNA recovered were compared with those derived from uncoated paper matrix 31-ETF (FIG. 4).

FIG. 4 shows DNA Recovery from FTA Cards as determined by quantitative PCR. DNA was applied to the matrices and recovered. The quantity of DNA recovered from FTA was compared with that recovered from uncoated paper. This graph demonstrates that recovery of DNA data from FTA is superior to recovery from a support which has no stabilising reagents added.

To enhance the usefulness of the invention the inventors propose means for monitoring the integrity of the DNA for example visually on the solid support, or by minor processing of a portion of the storage medium (to leave the bulk of the replicated data on the storage medium).

In one embodiment, the data integrity monitoring technique relies on specific reporter groups attached or incorporated into the synthesized DNA either during or post synthesis. The reporters will generate an appropriate signal to indicate DNA integrity e.g. if the DNA remains intact or has become degraded. Such reporter groups could potentially be based upon a range of molecules including florescent cye-dyes, quenchers and emitters, enzymatic reporters etc. If florescent dyes are used, then simple illumination of the storage medium will indicate the integrity of the data stored thereon. Alternatively the data integrity monitoring technique may be performed by removing a portion of the storage medium and performing short tandem repeat (STR) profiling reaction that will interrogate 20 or so different STR loci generated as control DNA sequences within the synthesised DNA data. Such interrogation should report the correct profile, if the integrity of the DNA data is intact. Either system will potentially facilitate a relatively simple method in which the integrity of the DNA can be monitored during/ after storage.

Example 3

Short Tandem Repeat Profiling as a Data Integrity Check

In order to further demonstrate the integrity of the DNA applied to the FTA following elution, short tandem repeat (STR) profiling was carried out using punches taken from dried blood spots on FTA Micro Cards. Dried blood spots for sample collection purposes were prepared as follows. Human whole blood, from 2 donors, (75 µl) was spotted on to FTA Micro Cards, allowed to dry at ambient temperature for 3 h, and stored in a desiccator before use. FTA cards were sampled within one week of spotting. FTA cards were punched at the centre of the sample spot in order to reduce variability.

The resultant punches were added directly to the STR profiling reagents and direct STR profiling was carried out on the punches using a PowerPlex 18D System (Promega, Southampton, UK) over 26 amplification cycles, following the kit manufacturer's instructions. Thermal cycling conditions were as follows: 96° C. for 2 min., then: 94° C. for 10 sec, 60° C. for 1 min for 26 cycles, then: 60° C. for 20 min, followed by a 4° C. rest.

The resulting PCR products were analysed on an ABI™ 3130xl Genetic Analyzer capillary electrophoresis system. The electrophoresis run cocktail mix was prepared using 1.0 μl of CC5 (Promega) internal lane standard plus 10.0 μl HiDi formamide per sample. Eleven microliters of run cocktail mix was added to 1.0 μl of sample. Instrument settings were as follows: injection time, 5 seconds; injection and run voltages, 3 kV; run time, 1,500 seconds with a G5 dye set. Results were evaluated with GeneMapper™ v3.2 software (Life Technologies, Paisley, UK).

FIG. 5 shows an electropherogram prepared in GeneMapper software following DNA amplification from dried blood spots on FTA Micro Cards. Punches were prepared a 1.2 mm manual micro-punch. STR analysis was carried out using the PowerPlex 18D kits over 26 amplification cycles. The resulting PCR amplicons were analysed using an Applied Biosystems 3130xl Genetic Analyser and GeneMapper v3.2 software. The ordinate shows relative fluorescence units (RFU) ranging from 2000-8000, with 8000 RFU showing full scale deflection. The abscissa shows base pairs. The figures below the peaks indicate the number of short tandem repeats associated with each allele. Periodical STR profiling reactions can be performed on the synthesised DNA applied to FTA cards and a quality measure such as peak heights etc. can be used to determine the quality and integrity of the applied synthetic DNA. The use of small 1.2 mm punches will potentially represent a preservation of DNA resource stored on FTA for long periods It can be concluded that using a STR profiling is a viable way to determine the integrity of DNA data stored on FTA cards.

Where reporter groups are used, these reporters may provide for visual (manual or automated) inspection of the solid support and the generation of a signal that indicates that the DNA remains intact to facilitate sequencing & hence data recovery. The following commercially-available florescent dyes that are known to interact with DNA and have been used in fluorescence microscopy; PicoGreen, SYBR Green, Acridine Orange, Bisbenzimide trihydrochloride, HOE-33342. Hoechst 33258, DAPI, Hoechst, Propidium Iodide etc. Visible dyes DNA binding dyes include; methylene blue, thionine etc Chen et al 2009 Nano Today, 4, 125-134 describes a FRET assay to monitor DNA stability. Plasmid DNA was double-labeled with QD (525 nm emission) and specific nucleic acid dyes complexed with Cy5. The QD donor drives energy transfer stepwise through the intermediate nucleic acid dye to the final acceptor Cy5. Incorporating reagent into the DNA polymer could also be used.

The combination of data in the form of DNA on a storage medium according to the invention, coupled with a simple system to measure its integrity is a viable solution to archiving complex digital information.

Figure 6:
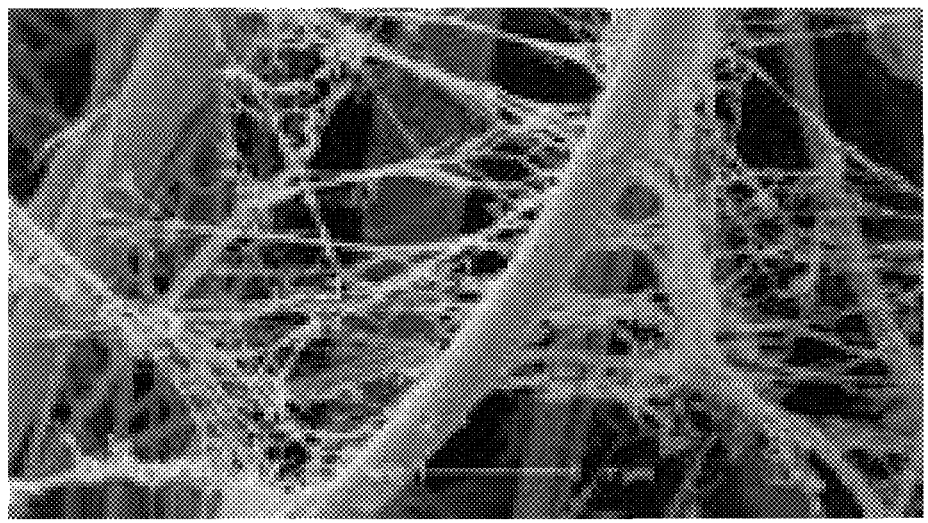
FIG. 6 shows a micrographic image of a data storage medium according to one embodiment of the invention.

FIG. 6 shows FTA paper having relatively large fibres of cellulose material i.e. those thick elements running generally from top to bottom of the picture, intertwined with DNA strands, akin to a spider's web. This image illustrates the way that the DNA is held to the FTA in an intertwined way and thereby stabilised.

The experiments above show that FTA is a preferred data storage medium, although previous experiments have concluded that a solid matrix in the form of a cellulose fibre paper matrix, which has no stabilising reagent added, is capable of storing human DNA for many years—27 years in the reported case. So, although desirable, it is not essential to include a stabilising reagent in or to the solid matrix.

Although fibrous solid matrix have been used in experiments—in this case a cellulose based paper product called FTA, it will be apparent to the skilled addressee that any material or surface which is man made and has a surface or subsurface having the ability to hold oligonucleotides in a similar manner to that shown in FIG. 6 could be employed as a solid matrix support for this invention. For example, woven or non-woven fibrous materials, including man made, or naturally occurring polymer fibres, mineral fibre based materials such as glass fibre materials, surface treated solid materials for example, chemically of mechanically treated materials, including laser etched surfaces, all provided with a surface micro roughness of sufficient roughness to hold DNA, porous materials such as porous polymers which have pores large enough to accommodate and hold the DNA stands, in a similar manner to that shown in FIG. 6. In each case the surface or subsurface of the material accommodates DNA, but will yield the DNA when required, and thereby is also capable of accepting a stabilising reagent if used in dry form or in wet form for subsequent drying.

Recovering DNA from the storage medium has been carried out in the experiments described above, using known techniques which all involve liquid based replication of DNA by PCR, although other replication is possible, for example isothermal amplification, e.g. helicase dependant amplification, or for example rolling circle amplification. However, providing sufficient DNA can be recovered from the storage medium, that liquid based replication is not essential.

Additionally, removal of a portion of the storage medium to recover data is not essential. It is possible to elute a portion of the DNA data off the storage medium without removing a portion of the storage medium itself. In a further example DNA can be removed for the storage medium by abrading the storage medium which will itself hold multiple copies of the DNA data, and analysing directly the material abraded from the storage medium. The DNA data could even be analysed whilst remaining on the storage medium, for example by spectroscopic, or molecular analysis techniques.

Although embodiments only have been illustrated, it will be apparent to the skilled addressee that further modifications, variants, additions and omissions are possible within the scope and spirit of the invention defined herein.

SEQUENCE LISTING

```
<160> NUMBER OF SEQ ID NOS: 3

<210> SEQ ID NO 1
<211> LENGTH: 3496
<212> TYPE: DNA
<213> ORGANISM: Artificial Sequence
<220> FEATURE:
```

<223> OTHER INFORMATION: puC19 plasmid vector having a fragment of Homo
     sapiens tumor protein p53, mRNA cloned in to the SmaI site of the
     puC19 plasmid

<400> SEQUENCE: 1

| | | | | | |
|---|---|---|---|---|---|
| gcgcccaata | cgcaaaccgc | ctctccccgc | gcgttggccg | attcattaat | gcagctggca | 60 |
| cgacaggttt | cccgactgga | aagcgggcag | tgagcgcaac | gcaattaatg | tgagttagct | 120 |
| cactcattag | gcaccccagg | ctttacactt | tatgcttccg | gctcgtatgt | tgtgtggaat | 180 |
| tgtgagcgga | taacaatttc | acacaggaaa | cagctatgac | catgattacg | ccaagcttgc | 240 |
| atgcctgcag | gtcgactcta | gaggatcccc | tccgtctggg | cttcttgcat | tctgggacag | 300 |
| ccaagtctgt | gacttgcacg | tactcccctg | ccctcaacaa | gatgttttgc | caactggcca | 360 |
| agacctgccc | tgtgcagctg | tgggttgatt | ccacaccccc | gcccggcacc | cgcgtccgcg | 420 |
| ccatggccat | ctacaagcag | tcacagcaca | tgacggaggt | tgtgaggcgc | tgcccccacc | 480 |
| atgagcgctg | ctcagatagc | gatggtctgg | cccctcctca | gcatcttatc | cgagtggaag | 540 |
| gaaatttgcg | tgtggagtat | ttggatgaca | gaaacacttt | tcgacatagt | gtggtggtgc | 600 |
| cctatgagcc | gcctgaggtt | ggctctgact | gtaccaccat | ccactacaac | tacatgtgta | 660 |
| acagttcctg | catgggcggc | atgaaccgga | ggcccatcct | caccatcatc | acactggaag | 720 |
| actccagtgg | taatctactg | ggacggaaca | gctttgaggt | gcgtgtttgt | gcctgtcctg | 780 |
| ggagagaccg | gcgcacagag | gaagagaatc | tccgcaagaa | aggggagcct | caccacgagc | 840 |
| tgccccagg | gagcactaag | cgagcactgc | caacaacac | cagctcctct | ccccagccaa | 900 |
| agaagaaacc | actggatgga | gaatatttca | cccttcagat | ccgtgggcgt | gagcgcttcg | 960 |
| agatgttccg | agagctgaat | gaggccttgg | aactcaagga | tgcccaggct | gggaaggagc | 1020 |
| cagggggag | cagggctcac | tccagccacc | tgaagtccaa | aaagggtcag | tctacctccc | 1080 |
| gggtaccgag | ctcgaattca | ctggccgtcg | ttttacaacg | tcgtgactgg | gaaaaccctg | 1140 |
| gcgttaccca | acttaatcgc | cttgcagcac | atccccctttt | cgccagctgg | cgtaatagcg | 1200 |
| aagaggcccg | caccgatcgc | ccttcccaac | agttgcgcag | cctgaatggc | gaatggcgcc | 1260 |
| tgatgcggta | ttttctcctt | acgcatctgt | gcggtatttc | acaccgcata | tggtgcactc | 1320 |
| tcagtacaat | ctgctctgat | gccgcatagt | taagccagcc | ccgacacccg | ccaacacccg | 1380 |
| ctgacgcgcc | ctgacgggct | tgtctgctcc | cggcatccgc | ttacagacaa | gctgtgaccg | 1440 |
| tctccgggag | ctgcatgtgt | cagaggtttt | caccgtcatc | accgaaacgc | gcgagacgaa | 1500 |
| agggcctcgt | gatacgccta | ttttttatagg | ttaatgtcat | gataataatg | gtttcttaga | 1560 |
| cgtcaggtgg | cacttttcgg | ggaaatgtgc | gcggaacccc | tatttgttta | tttttctaaa | 1620 |
| tacattcaaa | tatgtatccg | ctcatgagac | aataaccctg | ataaatgctt | caataatatt | 1680 |
| gaaaaaggaa | gagtatgagt | attcaacatt | tccgtgtcgc | ccttattccc | ttttttgcgg | 1740 |
| cattttgcct | tcctgttttt | gctcacccag | aaacgctggt | gaaagtaaaa | gatgctgaag | 1800 |
| atcagttggg | tgcacgagtg | ggttacatcg | aactggatct | caacagcggt | aagatccttg | 1860 |
| agagttttcg | ccccgaagaa | cgttttccaa | tgatgagcac | ttttaaagtt | ctgctatgtg | 1920 |
| gcgcggtatt | atcccgtatt | gacgccggc | aagagcaact | cggtcgccgc | atacactatt | 1980 |
| ctcagaatga | cttggttgag | tactcaccag | tcacagaaaa | gcatcttacg | gatggcatga | 2040 |
| cagtaagaga | attatgcagt | gctgccataa | ccatgagtga | taacactgcg | gccaacttac | 2100 |
| ttctgacaac | gatcggagga | ccgaaggagc | taaccgcttt | tttgcacaac | atggggatc | 2160 |
| atgtaactcg | ccttgatcgt | tgggaaccgg | agctgaatga | agccatacca | aacgacgagc | 2220 |

```
gtgacaccac gatgcctgta gcaatggcaa caacgttgcg caaactatta actggcgaac    2280
tacttactct agcttcccgg caacaattaa tagactggat ggaggcggat aaagttgcag    2340
gaccacttct gcgctcggcc cttccggctg gctggtttat tgctgataaa tctggagccg    2400
gtgagcgtgg gtctcgcggt atcattgcag cactggggcc agatggtaag ccctcccgta    2460
tcgtagttat ctacacgacg gggagtcagg caactatgga tgaacgaaat agacagatcg    2520
ctgagatagg tgcctcactg attaagcatt ggtaactgtc agaccaagtt tactcatata    2580
tactttagat tgatttaaaa cttcattttt aatttaaaag gatctaggtg aagatccttt    2640
ttgataatct catgaccaaa atcccttaac gtgagttttc gttccactga gcgtcagacc    2700
ccgtagaaaa gatcaaagga tcttcttgag atcctttttt tctgcgcgta atctgctgct    2760
tgcaaacaaa aaaaccaccg ctaccagcgg tggtttgttt gccggatcaa gagctaccaa    2820 ctcttttttcc gaaggtaact ggcttcagca gagcgcagat accaaatact gttcttctag    2880
tgtagccgta gttaggccac cacttcaaga actctgtagc accgcctaca tacctcgctc    2940
tgctaatcct gttaccagtg gctgctgcca gtggcgataa gtcgtgtctt accgggttgg    3000
actcaagacg atagttaccg gataaggcgc agcggtcggg ctgaacgggg gttcgtgca    3060 cacagcccag cttggagcga acgacctaca ccgaactgag atacctacag cgtgagctat    3120
gagaaagcgc cacgcttccc gaagggagaa aggcggacag gtatccggta agcggcaggg    3180
tcggaacagg agagcgcacg agggagcttc caggggggaaa cgcctggtat ctttatagtc    3240
ctgtcgggtt tcgccacctc tgacttgagc gtcgattttt gtgatgctcg tcaggggggc    3300
ggagcctatg gaaaaacgcc agcaacgcgg cctttttacg gttcctggcc ttttgctggc    3360
cttttgctca catgttcttt cctgcgttat cccctgattc tgtggataac cgtattaccg    3420
cctttgagtg agctgatacc gctcgccgca gccgaacgac cgagcgcagc gagtcagtga    3480
gcgaggaagc ggaaga                                                    3496
```

<210> SEQ ID NO 2
<211> LENGTH: 913
<212> TYPE: DNA
<213> ORGANISM: Artificial Sequence
<220> FEATURE:
<223> OTHER INFORMATION: Polymerase chain reaction product of puC19
      plasmid vector having a fragment of Homo sapiens tumor protein
      p53, mRNA cloned in to the SmaI site of the puC19 plasmid

<400> SEQUENCE: 2

```
caggaaacag ctatgaccat gattacgcca agcttgcatg cctgcaggtc gactctagag     60
gatcccctcc gtctgggctt cttgcattct gggacagcca agtctgtgac ttgcacgtac    120
tccctgcccc tcaacaagat gttttgccaa ctggccaaga cctgccctgt gcagctgtgg    180
gttgattcca caccccgcc cggcacccgc gtccgcgcca tggccatcta caagcagtca    240
cagcacatga cggaggttgt gaggcgctgc ccccaccatg agcgctgctc agatagcgat    300
ggtctggccc ctcctcagca tcttatccga gtggaaggaa atttgcgtgt ggagtatttg    360
gatgacagaa acacttttcg acatagtgtg gtggtgccct atgagccgcc tgaggttggc    420
tctgactgta ccaccatcca ctacaactac atgtgtaaca gttcctgcat gggcggcatg    480
aaccggaggc ccatcctcac catcatcaca ctggaagact ccagtggtaa tctactggga    540
cggaacagct ttgaggtgcg tgtttgtgcc tgtcctggga gaccggcg cacagaggaa    600 gagaatctcc gcaagaaagg ggagcctcac cacgagctgc ccccagggag cactaagcga    660
```

```
gcactgccca acaacaccag ctcctctccc cagccaaaga agaaaccact ggatggagaa        720
tatttcaccc ttcagatccg tgggcgtgag cgcttcgaga tgttccgaga gctgaatgag        780
gccttggaac tcaaggatgc ccaggctggg aaggagccag gggggagcag ggctcactcc        840
agccacctga agtccaaaaa gggtcagtct acctcccggg taccgagctc gaattcactg        900
gccgtcgttt tac                                                           913

<210> SEQ ID NO 3
<211> LENGTH: 200
<212> TYPE: DNA
<213> ORGANISM: Artificial Sequence
<220> FEATURE:
<223> OTHER INFORMATION: Polymerase chain reaction product of puC19
      plasmid vector having a fragment of Homo sapiens tumor protein
      p53, mRNA cloned in to the SmaI site of the puC19 plasmid

<400> SEQUENCE: 3
gcgcacagag gaagagaatc tccgcaagaa aggggagcct caccacgagc tgcccccagg         60
gagcactaag cgagcactgc ccaacaacac cagctcctct ccccagccaa agaagaaacc        120
actggatgga gaatatttca cccttcagat ccgtgggcgt gagcgcttcg agatgttccg        180
agagctgaat gaggccttgg                                                    200
```

The invention claimed is:

1. A data storage medium comprising a solid support matrix adapted for use as a dry storage support for non-naturally occurring oligonucleotide sequences encoded with ternary or quaternary base system DNA data,
  wherein the matrix is fibrous,
  wherein said matrix includes a reagent mix in a dry form comprising a combination of a weak base, a chelating agent, a stabilising reagent, and an anionic surfactant,
  wherein the stabilising reagent comprises a chaotropic salt, and
  wherein the storage medium includes a visual delineation around an area for holding the DNA data comprising: (i) a printed boundary on the fibrous matrix configured to show where the DNA data is stored to facilitate sampling therefrom or (ii) an indicating dye of chlorophenol red or phenol red which is configured to discolour, thereby showing where the DNA data is stored on the storage medium to facilitate sampling therefrom.

2. The data storage medium as claimed in claim 1, wherein the matrix comprises cellulose or glass fibres formed into a support of sufficient strength to hold the oligonucleotide sequences.

3. The data storage medium as claimed in claim 1, wherein the weak base is a Lewis base which has a pH of about 6 to 10.

4. The data storage medium as claimed in claim 3, wherein the weak base comprises an alkali metal carbonate, bicarbonate, phosphate or borate.

5. The data storage medium as claimed in claim 3, wherein the weak base comprises tris-hydroxymethyl amino methane (Tris), ethanolamine, triethanolamine, or glycine and alkaline salts of organic acids.

6. The data storage medium as claimed in claim 5, wherein the chelating agent comprises EDTA.

7. The data storage medium as claimed in claim 6, wherein the anionic surfactant includes a hydrocarbon moiety, aliphatic or aromatic, containing one or more anionic groups.

8. The data storage medium as claimed in claim 7, wherein the anionic surfactant comprises sodium dodecyl sulphate (SDS) and/or sodium lauryl sarcosinate (SLS).

9. A method of storing data, said method comprising the following steps:
  a) producing synthesised oligonucleotides having a non-naturally occurring nucleotide sequence representative of ternary or quaternary base system data to be stored;
  b) optionally replicating said oligonucleotides; and
  c) depositing said oligonucleotides, optionally replicated, onto a storage medium according to claim 1.

10. The method of storing data as claimed in claim 9, wherein at least steps b) and c) are performed in a liquid, and said liquid is allowed or caused to evaporate from the storage medium.

11. The method of storing data as claimed in claim 9, wherein step a) includes converting binary data into a quaternary code, and sequencing DNA nucleotides, according to the quaternary code to provide said oligonucleotides.

12. The method of storing data as claimed in claim 9, wherein step a) includes incorporating a reporter into said sequence, to provide an indication of data integrity, said reporter providing an increase or decrease in detectability in response to a change in said integrity.

13. The method of storing data as claimed in claim 12, wherein said reporter is a fluorescent dye.

14. The method of storing data as claimed in claim 13, wherein said nucleotide sequence is at least 250 base pairs in length.

15. The method of storing data as claimed in claim 14, wherein said replication is by means of a polymerase chain reaction (PCR), isothermal amplification, or rolling circle amplification.

16. The method of storing data as claimed in claim 15, wherein one or more sequences which aid replication are added to the end or ends of the sequenced oligonucleotides.

17. A method for recovering stored data from the storage medium of claim 1 when stored on the storage medium, said recovery method comprising the steps of:

i) extracting at least a portion of the replicated oligonucleotides from the storage medium;
ii) optionally performing further replication of said oligonucleotides; and
iii) performing an analysis of the oligonucleotides to determine their nucleotide sequence, and decoding said sequence to thereby recover said stored data.

18. The method for recovering stored data as claimed in claim 17, wherein said extracting step includes removing at least a portion of the storage medium or the DNA stored thereon, and introducing into a vessel the at least a portion, or DNA, and then performing said further replication step.

19. The method as claimed in claim 18, wherein said further replication step includes: adding a liquid to said at least a portion.

20. The method for recovering stored data from the storage medium, as claimed in claim 17, wherein the analysis step includes determining the nucleic composition of the oligonucleotide by known techniques, using: an electropherogram; radiolabelling; single-molecule real-time sequencing; pyrosequencing; sequencing by ligation; or dideoxy chain termination.

21. A method for determining integrity of non-naturally occurring oligonucleotide sequences encoded with ternary or quaternary base system DNA data stored on a storage medium comprising a solid support matrix, wherein the matrix is fibrous, wherein said matrix includes a reagent mix in a dry form, wherein the reagent mix comprises a combination of a weak base, a chelating agent, a stabilising reagent comprising a chaotropic salt, and an anionic surfactant, and wherein the storage medium includes a visual delineation around an area for holding the DNA data comprising: (i) a printed boundary on the fibrous matrix configured to show where the DNA data is stored or (ii) an indicating dye such as chlorophenol red or phenol red, which is configured to discolor, thereby showing where the DNA data is stored on the storage medium, said method including the steps of:

sampling medium from the visual delineated area; and performing an STR (short tandem repeat) profile analysis on a portion of the DNA data stored on the medium sampled from the visual delineated area.

* * * * *